(12) United States Patent
Nam et al.

(10) Patent No.: US 8,748,422 B2
(45) Date of Patent: Jun. 10, 2014

(54) PHARMACEUTICAL COMPOSITIONS CONTAINING QUINAZOLINE DERIVATIVES FOR TREATING AS SEROTONIN RECEPTOR ANTAGONIST

(75) Inventors: Ghil Soo Nam, Seoul (KR); Hye Whon Rhim, Seoul (KR); Ae Nim Pae, Seoul (KR); Hyun Ah Choo, Seoul (KR); Kyung Il Choi, Seoul (KR); Seung Yeol Nah, Seoul (KR)

(73) Assignee: Korea Institute of Science and Technology, Seoul (KR)

( * ) Notice: Subject to any disclaimer, the term of this patent is extended or adjusted under 35 U.S.C. 154(b) by 878 days.

(21) Appl. No.: 12/195,951

(22) Filed: Aug. 21, 2008

(65) Prior Publication Data

US 2009/0054433 A1 Feb. 26, 2009

(30) Foreign Application Priority Data

Aug. 22, 2007 (KR) ........................ 10-2007-0084322

(51) Int. Cl.
*A61K 31/5377* (2006.01)
*A61K 31/517* (2006.01)
*A61P 25/00* (2006.01)

(52) U.S. Cl.
USPC .................................. 514/234.8; 514/266.3

(58) Field of Classification Search
USPC .......................................... 514/234.8, 266.3
See application file for complete search history.

(56) References Cited

FOREIGN PATENT DOCUMENTS

KR 100749843 B1 8/2007

OTHER PUBLICATIONS

Mi et al (Novel T-type calcium channel blockers: Dioxoquinazoline carboxaminde derivatives, Bioorganic & Medicinal Chemistry, 15 (2007) 365-373.*
Dooley et al (Ca2+ channel α2δ Ligands: novel modulators of neurotransmission, TREANDS in Pharmacological Sciences, vol. 28, No. 2, p. 75-82).*
Marisela Morales, et al., "Differential Composition of 5-Hydroxytryptamine3 Receptors Synthesized in the Rat CNS and Peripheral Nervous System", Journal, Aug. 1, 2002, pp. 6732-6741.
Laramie M. Gaster, et al., "Serotonin 5-HT3 and 5-HT4 Receptor Antagonists", 1997, pp. 163-214, vol. 17, No. 2.
Nicholas M. Barnes, et al., "A Review of Central 5-HT Receptors and Their Function",1999, pp. 1083-1152.
Herbert Y. Meltzer, M.D., "The Role of Serotonin in Antipsychotic Drug Action", 1999, pp. 106S-115S, vol. 21, No. 2S.
Laurence H. Tecott, et al., "Nervous System Distribution of the Serotonin 5-HT3 Receptor mRNA", pp. 1430-1434, vol. 90.
Andres V. Maricq, et al., "Primary Structure and Functional Expression of the 5HT3 Receptor, a Serotonin-Gated Ion Channel", pp. 432-435, vol. 254.

* cited by examiner

*Primary Examiner* — San-Ming Hui
*Assistant Examiner* — Kathrien Cruz
(74) *Attorney, Agent, or Firm* — William E. Beaumont

(57) ABSTRACT

The present invention relates to a pharmaceutical composition containing one or more quinazoline compounds as an active ingredient, which has antagonistic activity against serotonin 5-HT$_3$A and is effective for the prevention and treatment of central nervous system (CNS) diseases, including emesis, nausea, alcoholism, drug abuse, depression, compulsive neurosis, anxiety, seizure, Alzheimer's disease, Parkinson's disease, Huntington's chorea, psychosis, schizophrenia, suicidal tendency, sleep disorder, appetite disorder and migraine.

10 Claims, No Drawings

PHARMACEUTICAL COMPOSITIONS CONTAINING QUINAZOLINE DERIVATIVES FOR TREATING AS SEROTONIN RECEPTOR ANTAGONIST

CROSS-REFERENCE TO RELATED APPLICATION

This application claims, under 35 U.S.C. §119(a), the benefit of Korean Patent Application No. 10-2007-0084322 filed Aug. 22, 2007, the entire contents of which are incorporated herein by reference.

BACKGROUND OF THE INVENTION

1. Field of the Invention

The present invention relates to a pharmaceutical composition containing one or more quinazoline derivatives as an active ingredient, which has antagonistic activity against serotonin 5-HT$_3$A and is effective for the prevention and treatment of central nervous system (CNS) diseases, including emesis, nausea, alcoholism, drug abuse, depression, compulsive neurosis, anxiety, seizure, Alzheimer's disease, Parkinson's disease, Huntington's chorea, psychosis, schizophrenia, suicidal tendency, sleep disorder, appetite disorder and migraine.

2. Description of the Background

Serotonin is known to play an important role in psychiatric disorders (e.g., depression, aggression, seizure, compulsive neurosis, psychosis, schizophrenia, suicidal tendency), degenerative nerve disorders (e.g., Alzheimer's disease, Parkinson's disease, Huntington's chorea, anorexia, polyphagia, insomnia, alcoholism-related disorders, cerebral vascular accidents, migraine, and various other pathologic conditions [Meltzer, *Neuropsychopharmacology*, 21:106S-115S (1999); Barnes & Sharp. *Neuropsychopharmacology*, 38:1083-1152 (1999): Glennon, *Neurosci. Biobehavioral Rev.*, 14:35(1990)]. Serotonin (5-hydroxytryptamine, or 5-HT) receptors are present in human and animals, and play an important role in physiological and behavioral functions. Until now, about 15 genetically different 5-HT receptor subtypes have been cloned. Each subtype exhibits unique distribution and shows various preference and relationships for different ligands.

A serotonin 5-HT$_3$ receptor is a ligand-gated ionotropic receptor which allows the passage of cations [Maricq et al, *Science*, 1991, 254, 432-437]. The 5-HT$_3$ receptor is mainly found in the human CNS [Morales, M et al, *J. Neurosci.*, 2002, 22, 6732-6741]. The 5-HT$_3$A receptor subtype was first cloned in 1991 by Maricq et al [Maricq et al, *Science*, 1991, 254, 432-437], and is found in the peripheral and limbic areas of the brain, including cortex, amygdala, hippocampus, and so forth [Tecott et al, *Pro. Natl. Acad. Sci.* U.S.A. 1993, 90, 1430-1434].

The 5-HT$_3$ receptor exists either as 5-HT$_3$A homomer or 5-HT$_3$A and 5-HT$_3$B heteromer. Both have the 5-HT$_3$A subtype and it is known that their function is mostly provided by 5-HT$_3$A. According to physiological studies on the 5-HT$_3$A receptor, ondansetron, granisetron, tropisetron, and the like are effective and selective antagonists of the receptor [Gaster et al, *Med. Res. Rev.* 1997, 17, 163-214]. Clinical researches on these compounds show that they provide excellent effect for the treatment or amelioration of emesis, nausea, etc., during the cancer chemotherapy. Further, the 5-HT$_3$A receptor is associated with alcoholism, drug abuse, depression, cognitive performance, psychological anxiety, pain, and the like [Silverston et al, *Exp. Opi. Ther. Patents* 1996, 6, 471-481].

SUMMARY OF THE INVENTION

The inventors of the present invention have discovered that the disclosed quinazoline derivatives described herein exhibit pharmacological antagonistic activity against serotonin 5-HT$_3$A, and these compounds and compositions containing the same provide superior preventive and therapeutic effects in related CNS diseases.

DETAILED DESCRIPTION OF THE PREFERRED EMBODIMENT

In one aspect, the present invention provides a pharmaceutical composition for the prevention and treatment of CNS diseases related to the serotonin 5-HT$_3$A receptor, which contains one or more quinazoline-based compounds or derivatives represented by the following Formula (1) or a pharmaceutically acceptable salt thereof as active ingredient:

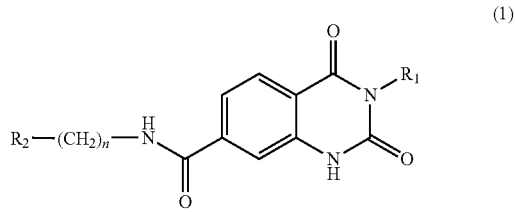

(1)

wherein
R$_1$ is hydrogen, C$_1$-C$_6$ alkyl, phenyl or benzyl,
R$_2$ is a heterocyclic group selected from morpholine, pyrrolidine and piperidine,
wherein the phenyl or benzyl of R$_1$ are optionally substituted by a substituent selected from halogen, C$_1$-C$_6$ alkyl and C$_1$-C$_6$ alkoxy, and
n is an integer from 1 to 6.
More preferably,
R$_1$ is hydrogen; methyl, ethyl, propyl, isopropyl, butyl, isobutyl, cyclobutyl, pentyl, isopentyl, cyclopentyl, hexyl, isohexyl, cyclohexyl; phenyl; phenyl substituted by a substituent selected from methyl, ethyl, propyl, isopropyl, butyl, isobutyl, cyclobutyl, pentyl, isopentyl, cyclopentyl, hexyl, isohexyl cyclohexyl, fluoro, chloro, bromo, iodo, methoxy, ethoxy, propoxy, butoxy, pentoxy and hexyloxy; benzyl; or benzyl substituted by a substituent selected from methyl, ethyl, propyl, isopropyl, butyl, isobutyl, cyclobutyl, pentyl, isopentyl, cyclopentyl, hexyl, isohexyl cyclohexyl, fluoro, chloro, bromo, iodo, methoxy, ethoxy, propoxy, butoxy, pentoxy and hexyloxy,
R$_2$ is morpholine, pyrrolidine or piperidine, and
n is an integer from 1 to 6.

Advantageous Effects

With superior antagonistic activity against serotonin 5-HT$_3$A, the quinazoline derivatives of the present invention represented by the Formula (1) are effective for the prevention and treatment of central nervous system (CNS) diseases.

Accordingly, the quinazoline derivatives of the present invention represented by Formula (1) are useful in a pharmaceutical composition or a health food composition for the prevention and treatment of central nervous system (CNS) diseases, including emesis, nausea, alcoholism, drug abuse, depression, compulsive neurosis, anxiety, seizure, Alzheimer's disease, Parkinson's disease, Huntington's chorea, psychosis, schizophrenia, suicidal tendency, sleep disorder, appetite disorder and migraine.

Preferred specific examples of the quinazoline-based compounds or derivatives represented by Formula (1) include:

3-(4-chloro-benzyl)-2,4-dioxo-1,2,3,4-tetrahydro-quinazoline-7-carboxylic acid (2-pyrrolidine-1-yl-ethyl)-amide,
3-(4-fluoro-phenyl)-2,4-dioxo-1,2,3,4-tetrahydro-quinazoline-7-carboxylic acid (2-piperidine-1-yl-ethyl)-amide,
3-(4-methoxy-phenyl)-2,4-dioxo-1,2,3,4-tetrahydro-quinazoline-7-carboxylic acid (2-piperidine-1-yl-ethyl)-amide,
3-(2-fluoro-benzyl)-2,4-dioxo-1,2,3,4-tetrahydro-quinazoline-7-carboxylic acid (2-piperidine-1-yl-ethyl)-amide,
3-(3-fluoro-benzyl)-2,4-dioxo-1,2,3,4-tetrahydro-quinazoline-7-carboxylic acid (2-piperidine-1-yl-ethyl)-amide,
3-(4-fluoro-benzyl)-2,4-dioxo-1,2,3,4-tetrahydro-quinazoline-7-carboxylic acid (2-piperidine-1-yl-ethyl)-amide,
3-(2-methoxy-benzyl)-2,4-dioxo-1,2,3,4-tetrahydro-quinazoline-7-carboxylic acid (2-piperidine-1-yl-ethyl)-amide,
3-(3-methoxybenzyl)-2,4-dioxo-1,2,3,4-tetrahydro-quinazoline-7-carboxylic acid (2-piperidine-1-yl-ethyl)-amide,
3-(4-methoxybenzyl)-2,4-dioxo-1,2,3,4-tetrahydro-quinazoline-7-carboxylic acid (2-piperidine-1-yl-ethyl)-amide,
3-cyclohexyl-2,4-dioxo-1,2,3,4-tetrahydro-quinazoline-7-carboxylic acid (2-piperidine-1-yl-ethyl)-amide,
2,4-dioxo-3-propyl-1,2,3,4-tetrahydro-quinazoline-7-carboxylic acid (2-piperidine-1-yl-ethyl)-amide,
3-methyl-2,4-dioxo-1,2,3,4-tetrahydro-quinazoline-7-carboxylic acid (2-piperidine-1-yl-ethyl)-amide,
(2-chloro-benzyl)-2,4-dioxo-1,2,3,4-tetrahydro-quinazoline-7-carboxylic acid (2-piperidine-1-yl-ethyl)-amide,
3-(4-chloro-benzyl)-2,4-dioxo-1,2,3,4-tetrahydro-quinazoline-7-carboxylic acid (2-piperidine-1-yl-ethyl)-amide,
3-(4-chloro-benzyl)-2,4-dioxo-1,2,3,4-tetrahydro-quinazoline-7-carboxylic acid (2-(2-methylpiperidine-1-yl)ethyl)-amide,
3-(4-chloro-benzyl)-2,4-dioxo-1,2,3,4-tetrahydro-quinazoline-7-carboxylic acid (3-morpholine-4-yl-propyl)-amide,
3-(4-chloro-benzyl)-2,4-dioxo-1,2,3,4-tetrahydro-quinazoline-7-carboxylic acid [3-(2-methyl-piperidine-1-yl)-propyl]-amide,
3-(4-chloro-benzyl)-2,4-dioxo-1,2,3,4-tetrahydro-quinazoline-7-carboxylic acid [3-(2-ethyl-piperidine-1-yl)-propyl]-amide, and
3-(4-chloro-benzyl)-2,4-dioxo-1,2,3,4-tetrahydro-quinazoline-7-carboxylic acid (3-piperidine-1-yl-propyl)-amide.

The quinazoline derivatives represented by Formula (1) can be prepared by a variety of preparation methods [Korean Patent Application No. 2006-0065975]. The present invention is characterized not by the derivatives or the preparation methods thereof, but by their superior inhibition effect against the 5-HT$_3$A receptor.

That is, the present invention can be applied to prevent and treat CNS diseases through antagonistic action against the 5-HT$_3$A receptor, specifically, emesis, nausea, alcoholism, drug abuse, depression, compulsive neurosis, anxiety, seizure, Alzheimer's disease, Parkinson's disease, Huntington's chorea, psychosis, schizophrenia, suicidal tendency, sleep disorder, appetite disorder, migraine, and the like.

The quinazoline derivatives represented by Formula (1) may be used in the form of a pharmaceutically acceptable salt. Preferably, the salt may be an acid adduct salt formed from a pharmaceutically acceptable free acid. The quinazoline derivative represented by Formula 1 may be prepared into a pharmaceutically acceptable acid adduct salt by the method commonly used in the related art. The free acid may be an organic or inorganic acid. Examples of the inorganic acid include hydrochloric acid, bromic acid, sulfuric acid, phosphoric acid, and the like. Examples of the organic acid include citric acid, acetic acid, lactic acid, tartaric acid, maleic acid, fumaric acid, formic acid, propionic acid, oxalic acid, trifluoroacetic acid, benzoic acid, gluconic acid, methanesulfonic acid, glycolic acid, succinic acid, 4-toluenesulfonic acid, galacturonic acid, embonic acid, glutamic acid, aspartic acid, and the like.

When the composition of the present invention is used as medicine, the quinazoline derivative represented by Formula (1) or a pharmaceutically acceptable salt thereof may be mixed with a vehicle commonly used in the pharmaceutical field and prepared into common preparation forms, for example, oral administration formulations such as tablet, capsule, troche, liquid, suspension, and the like; injection formulations such as solution or suspension for injection, dry powder for injection which can be used immediately by dissolving in distilled water for injection, and the like; or various other formulations including ointment. The pharmaceutical formulations prepared by using a commonly used vehicle may be administered orally or parenterally, for example, intravenously, subcutaneously, intra-abdominally or locally. The dose of the quinazoline derivative represented by Formula 1 according to the present invention may vary depending on the patient's age, physical conditions, and the like. In general, for an adult, 10 to 500 mg, preferably 50 to 300 mg, is administered per day. Depending on the decision of a pharmacist or a doctor, it may be administered several times, preferably once to 6 times, a day.

As used herein, health food refers to a food prepared into capsule, powder, suspension, and the like by adding the quinazoline derivative represented by Formula 1. It is intended to provide specific good effects on health, but, differently from medicines, it is made from food and is without adverse reactions, which may occur during long-term taking of medicines.

Specifically, the food may be confectionery, processed foods, dairy products, drinks, or the like, and may be in any form, without particular limitation. For example, the health food may be in the form of solid, semisolid, gel, liquid, powder, and the like.

For clinical purposes, the composition comprising the quinazoline derivative represented by Formula 1 as active ingredient may be administered orally or parenterally. The composition may be in the form of general medicines, quasi-drugs, health foods, and the like.

The following examples further illustrate the present invention and are not intended to limit the same.

The quinazoline derivatives of the present invention may be known methods. Screening of activity was carried out in order to confirm the use of the compounds for treatment of new diseases.

EXAMPLES

The following examples illustrate the invention and are not intended to limit the same.

Example 1

3-(4-Chloro-benzyl)-2,4-dioxo-1,2,3,4-tetrahydro-quinazoline-7-carboxylic acid (2-pyrrolidine-1-yl-ethyl)-amide (Compound 1)

Dimethyl 2-aminoterephthalate (3.54 g, 16.9 mmol) was dissolved in 1,4-dioxane. After adding triethylamine (5.8 mL, 42.3 mmol) and 1-chloro-4-isonatomethylbenzene (2.9 mL, 22.0 mmol), stirring was carried out at 90° C. under reflux for 3-4 days. After the reaction was completed, the produced solid was filtered with ether to obtain 2.38 g (41%) of 3-(4-chloro-benzyl)-2,4-dioxo-1,2,3,4-tetrahydroquinazoline-7-carboxylic acid methyl ester.

$^1$H NMR (300 MHz, DMSO-$d_6$) δ 11.73 (s, 1H), 8.06 (d, J=8.2 Hz, 1H), 7.79 (s, 1H), 7.71 (d, J=8 Hz, 1H), 7.36 (bs, 4H), 5.06 (s, 2H), 3.89 (s, 3H).

Thus obtained ester (2.54 g, 7.4 mmol) was dissolved in 10% NaOH/1,4-dioxane (¼, w/w) at room temperature and stirred for 1 hour. After the reaction was completed, white solid produced by acidification with strong hydrochloric acid was filtered to obtain 2.22 g (91%) of 3-(4-chloro-benzyl)-2,4-dioxo-1,2,3,4-tetrahydroquinazoline-7-carboxylic acid.

$^1$H NMR (300 MHz, DMSO-$d_6$) δ 13.52 (s, 1H), 11.73 (s, 1H), 8.02 (d, J=8.2 Hz, 1H), 7.78 (s, 1H), 7.69 (d, J=8.2 Hz, 1H), 7.36 (bs, 4H), 5.07 (s, 2H).

Thus obtained acid (90 mg, 0.272 mol) was dissolved in $SOCl_2$ (4 mL) and stirred at 85° C. for 2 hours under reflux. The resultant compound was concentrated under reduced pressure. After maintaining at vacuum status for about 8 hours, the compound was dissolved in purified $CH_2Cl_2$ (4 mL) and 2-pyrrolidine-1-yl-ethylamine (76 mL, 0.598 mmol) was slowly added dropwise at 0° C. Then, stirring was carried out at room temperature for 2 hours. After concentration under reduced pressure, the concentrate was filtered through silica gel chromatography ($CH_2Cl_2$:MeOH=10:1) to obtain 69 mg (59%) of the target compound.

$^1$H NMR (400 MHz, DMSO-$d_6$) δ 11.67 (s, 1H), 8.66 (bs, 1H), 7.98 (d, J=8.1 Hz, 1H), 7.60-7.57 (m, 2H), 7.27 (bs, 4H), 5.05 (s, 2H), 3.37-3.34 (m, 2H), 2.57 (bs, 6H), 1.66 (bs, 4H).

Example 2

3-(4-Fluoro-phenyl)-2,4-dioxo-1,2,3,4-tetrahydro-quinazoline-7-carboxylic acid (2-piperidine-1-yl-ethyl)-amide (Compound 2)

4.1 g (90%) of 3-(4-fluoro-phenyl)-2,4-dioxo-1,2,3,4-tetrahydro-quinazoline-7-carboxylic acid methyl ester was obtained in the same manner of Example 1, using dimethyl 2-aminoterephthalate (3.0 g, 14.3 mmol), triethylamine (0.5 mL, 3.6 mmol) and 1-fluoro-4-isocyanato-benzene (3.0 mL, 26.4 mmol).

$^1$H NMR (300 MHz, DMSO-$d_6$) δ 11.76 (s, 1H), 8.06 (d, J=8.2 Hz, 1H), 7.81 (s, 1H), 7.74 (dd, J=8.2 Hz, J=1.2 Hz, 1H), 7.443-7.39 (m, 2H), 7.35-7.29 (m, 2H), 3.92 (s, 3H).

From thus obtained ester (4.08 g, 13.0 mmol), 3.41 g (88%) of 3-(4-fluoro-phenyl)-2,4-dioxo-1,2,3,4-tetrahydro-quinazoline-7-carboxylic acid was obtained in the same manner of Example 1.

$^1$H NMR (300 MHz, DMSO-$d_6$) δ 13.58 (s, 1H), 11.87 (s, 1H), 8.02 (d, J=8.2 Hz, 1H), 7.85 (s, 1H), 7.71 (dd, J=8.2 Hz, J=1.2 Hz, 1H), 7.43-7.38 (m, 2H), 7.35-7.29 (m, 2H).

From thus obtained acid (99 mg, 0.329 mmol), 45 mg (34%) of the target compound was obtained in the same manner of Example 1, using 2-piperidine-1-yl-ethylamine (70 mL, 0.495 mmol).

$^1$H NMR (300 MHz, CD$_3$OD) δ 8.13 (d, J=8.2 Hz, 1H), 7.66-7.61 (m, 2H), 7.38-7.33 (m, 2H), 7.28-7.22 (m, 2H), 3.59 (t, J=6.8 Hz, 2H), 2.65-2.61 (m, 6H), 1.70-1.62 (m, 4H), 1.53-1.51 (m, 2H).

Example 3

3-(4-Methoxy-phenyl)-2,4-dioxo-1,2,3,4-tetrahydro-quinazoline-7-carboxylic acid (2-piperidine-1-yl-ethyl)-amide (Compound 3)

3.6 g (76%) of 3-(4-methoxy-phenyl)-2,4-dioxo-1,2,3,4-tetrahydro-quinazoline-7-carboxylic acid methyl ester was obtained in the same manner of Example 1, using dimethyl 2-aminoterephthalate (3.0 g, 14.3 mmol), triethylamine (0.20 mL, 1.4 mmol) and 1-isocyanato-4-methoxy-benzene (3.0 mL, 23.7 mmol).

$^1$H NMR (300 MHz, DMSO-$d_6$) δ 11.72 (s, 1H), 8.05 (d, J=8.2 Hz, 1H), 7.80 (s, 1H), 7.72 (dd, J=8.2 Hz, J=1.3 Hz, 1H), 7.24 (d, J=8.8 Hz, 2H), 7.02 (d, J=8.8 Hz, 2H), 3.91 (s, 3H), 3.81 (s, 3H).

From thus obtained ester (3.56 g, 10.91 mmol), 3.40 g (99%) of 3-(4-methoxy-phenyl)-2,4-dioxo-1,2,3,4-tetrahydro-quinazoline-7-carboxylic acid was obtained in the same manner of Example 1.

$^1$H NMR (400 MHz, DMSO-$d_6$) δ 13.56 (s, 1H), 11.69 (s, 1H), 8.01 (d, J=8.2 Hz, 1H), 7.81 (s, 1H), 7.69 (d, J=8.2 Hz, 1H), 7.22 (d, J=8.4 Hz, 2H), 7.01 (d, J=8.4 Hz, 2H), 3.80 (s, 3H).

From thus obtained acid (100 mg, 0.320 mmol), 45 mg (33%) of the target compound was obtained in the same manner of Example 1, using 2-piperidine-1-yl-ethylamine (82 mL, 0.576 mmol).

$^1$H NMR (300 MHz, DMSO-$d_6$) δ 11.62 (s, 1H), 8.61 (t, J=4.9 Hz, 1H), 8.00 (d, J=8.2 Hz, 1H), 7.63 (s, 1H), 7.58 (d, J=8.2 Hz, 1H), 7.22 (d, J=8.8 Hz, 2H), 7.01 (d, J=8.8 Hz, 2H), 3.81 (s, 3H), 3.41-3.35 (t, 2H), 2.42 (bs, 2H), 2.40 (bs, 4H), 1.48 (bs, 4H), 1.38 (bs, 2H).

Example 4

3-(2-Fluoro-benzyl)-2,4-dioxo-1,2,3,4-tetrahydro-quinazoline-7-carboxylic acid (2-piperidine-1-yl-ethyl)-amide (Compound 4)

3.17 g (67%) of 3-(2-fluoro-benzyl)-2,4-dioxo-1,2,3,4-tetrahydro-quinazoline-7-carboxylic acid methyl ester was obtained in the same manner of Example 1, using dimethyl 2-aminoterephthalate (3.0 g, 14.3 mmol), triethylamine (1.9 mL, 1.4 mmol) and 1-fluoro-2-isocyanatomethyl-benzene (2.4 mL, 18.7 mmol).

$^1$H NMR (300 MHz, DMSO-$d_6$) δ 11.78 (s, 1H), 8.09 (d, J=8.2 Hz, 1H), 7.84 (s, 1H), 7.76 (d, J=8.2 Hz, 1H), 7.34-7.27 (m, 1H), 7.23-7.17 (m, 2H), 7.13-7.08 (m, 1H), 5.10 (s, 2H), 3.91 (s, 3H).

From thus obtained ester (3.12 g, 9.5 mmol), 2.84 g (98%) of 3-(2-fluoro-benzyl)-2,4-dioxo-1,2,3,4-tetrahydro-quinazoline-7-carboxylic acid was obtained in the same manner of Example 1.

¹H NMR (300 MHz, DMSO-d₆) δ 13.56 (s, 1H), 11.77 (s, 1H), 8.03 (d, J=8.2 Hz, 1H), 7.80 (s, 1H), 7.71 (dd, J=8.2 Hz, J=1.2 Hz, 1H), 7.34-7.27 (m, 1H), 7.23-7.08 (m, 3H), 5.14 (s, 2H).

From thus obtained acid (99 mg, 0.315 mmol), 35 mg (53%) of the target compound was obtained in the same manner of Example 1, using 2-piperidine-1-yl-ethylamine (67 mL, 0.472 mmol).

¹H NMR (400 MHz, DMSO-d₆) δ 11.77 (s, 1H), 10.14 (s, 1H), 9.13 (bs, 1H), 8.00 (d, J=7.9 Hz, 1H), 7.72-7.68 (m, 2H), 7.30-7.28 (m, 1H), 7.20-7.16 (m, 1H), (m, 1H), 7.11-7.07 (m, 1H), 5.13 (s, 2H), 3.67 (bs, 2H), 3.49 (bs, 2H), 3.21 (bs, 2H), 1.78 (bs, 4H), 1.71-1.67 (m, 2H).

Example 5

3-(3-Fluoro-benzyl)-2,4-dioxo-1,2,3,4-tetrahydro-quinazoline-7-carboxylic acid (2-piperidine-1-yl-ethyl)-amide (Compound 5)

3.14 g (67%) of 3-(3-fluoro-benzyl)-2,4-dioxo-1,2,3,4-tetrahydro-quinazoline-7-carboxylic acid methyl ester was obtained in the same manner of Example 1, using dimethyl 2-aminoterephthalate (3.0 g, 14.3 mmol), triethylamine (0.9 mL, 0.7 mmol) and 1-fluoro-3-isocyanatomethyl-benzene (3.2 mL, 22.0 mmol).

¹H NMR (300 MHz, DMSO-d₆) δ 11.76 (s, 1H), 8.07 (d, J=8.2 Hz, 1H), 7.79 (s, 1H), 7.72 (dd, J=8.2 Hz, J=1.2 Hz, 1H), 7.39-7.32 (m, 1H), 7.17-7.06 (m, 3H), 5.09 (s, 2H), 3.90 (s, 3H).

From thus obtained ester (3.10 g, 9.4 mmol), 2.67 g (90%) of 3-(3-fluoro-benzyl)-2,4-dioxo-1,2,3,4-tetrahydro-quinazoline-7-carboxylic acid was obtained in the same manner of Example 1.

¹H NMR (300 MHz, DMSO-d₆) δ 13.53 (s, 1H), 11.75 (s, 1H), 8.04 (d, J=8.2 Hz, 1H), 7.79 (s, 1H), 7.70 (dd, J=8.2 Hz, J=1.3 Hz, 1H), 7.39-7.32 (m, 1H), 7.17-7.05 (m, 3H), 5.10 (s, 2H).

From thus obtained acid (99 mg, 0.315 mmol), 35 mg (26%) of the target compound was obtained in the same manner of Example 1, using 2-piperidine-1-yl-ethylamine (67 mL, 0.472 mmol).

¹H NMR (400 MHz, DMSO-d₆) δ 11.69 (s, 1H), 8.62 (bs, 1H), 7.99 (d, J=8.2 Hz, 1H), 7.60-7.56 (m, 2H), 7.37-7.31 (m, 1H), 7.14-7.12 (m, 2H), 7.09-7.05 (m, 1H), 5.08 (s, 2H), 3.37 (bs, 2H), 2.40 (bs, 6H), 1.48 (bs, 4H), 1.36 (bs, 2H).

Example 6

3-(4-Fluoro-benzyl)-2,4-dioxo-1,2,3,4-tetrahydro-quinazoline-7-carboxylic acid (2-piperidine-1-yl-ethyl)-amide (Compound 6)

3.26 g (74%) of 3-(4-fluoro-benzyl)-2,4-dioxo-1,2,3,4-tetrahydro-quinazoline-7-carboxylic acid methyl ester was obtained in the same manner of Example 1, using dimethyl 2-aminoterephthalate (2.8 g, 13.0 mmol), triethylamine (0.9 mL, 0.7 mmol) and 1-fluoro-4-isocyanatomethyl-benzene (2.6 mL, 20.0 mmol).

¹H NMR (300 MHz, DMSO-d₆) δ 11.75 (s, 1H), 8.08 (d, J=8.2 Hz, 1H), 7.84 (s, 1H), 7.72 (dd, J=8.2 Hz, J=1.2 Hz, 1H), 7.42-7.37 (m, 2H), 7.16-7.10 (m, 2H), 5.06 (s, 2H), 3.90 (s, 3H).

From thus obtained ester (3.22 g, 9.8 mmol), 3.05 g (97%) of 3-(4-fluoro-benzyl)-2,4-dioxo-1,2,3,4-tetrahydro-quinazoline-7-carboxylic acid was obtained in the same manner of Example 1.

¹H NMR (300 MHz, DMSO-d₆) δ 13.53 (s, 1H), 11.75 (s, 1H), 8.05 (d, J=8.2 Hz, 1H), 7.78 (s, 1H), 7.70 (dd, J=8.2 Hz, J=1.4 Hz, 1H), 7.41-7.36 (m, 2H), 7.16-7.10 (m, 2H), 5.06 (s, 2H).

From thus obtained acid (99 mg, 0.315 mmol), 60 mg (45%) of the target compound was obtained in the same manner of Example 1, using 2-piperidine-1-yl-ethylamine (67 mL, 0.472 mmol).

¹H NMR (400 MHz, DMSO-d₆) δ 11.66 (s, 1H), 8.59 (bs, 1H), 7.98 (d, J=8.1 Hz, 1H), 7.59-7.55 (m, 2H), 7.39-7.35 (m, 2H), 5.05 (s, 2H), 3.34 (bs, 2H), 2.43-2.35 (m, 6H), 1.46 (bs, 4H), 1.35 (bs, 2H).

Example 7

3-(2-Methoxy-benzyl)-2,4-dioxo-1,2,3,4-tetrahydro-quinazoline-7-carboxylic acid (2-piperidine-1-yl-ethyl)-amide (Compound 7)

4.0 g (83%) of 3-(2-methoxybenzyl)-2,4-dioxo-1,2,3,4-tetrahydro-quinazoline-7-carboxylic acid methyl ester was obtained in the same manner of Example 1, using dimethyl 2-aminoterephthalate (3.0 g, 14.3 mmol), triethylamine (0.6 mL, 4.3 mmol) and 1-(isocyanatomethyl)-2-methoxybenzene (3.9 mL, 25.7 mmol).

¹H NMR (300 MHz, DMSO-d₆) δ 11.76 (s, 1H), 8.07 (d, J=8.2 Hz, 1H), 7.81 (s, 1H), 7.72 (d, J=8.1 Hz, 1H), 7.21 (bs, 1H), 7.01 (d, J=8.0 Hz, 1H), 6.82 (bs, 2H), 5.04 (s, 2H), 3.91 (s, 3H), 3.78 (s, 3H).

From thus obtained ester (4.0 g, 11.84 mmol), 2.9 mg (75%) of 3-(2-methoxybenzyl)-2,4-dioxo-1,2,3,4-tetrahydro-quinazoline-7-carboxylic acid was obtained in the same manner of Example 1.

¹H NMR (300 MHz, DMSO-d₆) δ 13.56 (s, 1H), 11.79 (s, 1H), 8.05 (d, J=8.2 Hz, 1H), 7.82 (s, 1H), 7.71 (dd, J=8.2 Hz, J=1.3 Hz, 1H), 7.25-7.19 (m, 1H), 7.01 (d, J=8.4 Hz, 1H), 6.82-6.81 (m, 2H), 5.04 (s, 2H), 3.78 (s, 3H).

Thus obtained acid (90 mg, 0.276 mmol) was dissolved in methylene chloride and stirred at room temperature after adding oxalyl chloride (0.5 ml) and 2 drops of dimethylformamide. Thus produced acyl chloride was concentrated under reduced pressure. After maintaining at vacuum status for about 8 hours, the compound was dissolved in purified methylene chloride (4 mL) and 2-piperidine-1-yl-ethylamine (78 µL, 0.552 mmol) was slowly added dropwise at 0° C. Then, stirring was carried out at room temperature for 2 hours. After concentration under reduced pressure, the concentrate was filtered through silica gel chromatography (CH₂Cl₂:MeOH=20:1) to obtain 21 mg (18%) of the target compound.

¹H NMR (300 MHz, DMSO-d₆) δ 11.70 (s, 1H), 8.62 (t, J=5.0 Hz, 1H), 8.00 (d, J=8.2 Hz, 1H), 7.63 (t, J=8.9 Hz, 2H), 7.23-7.19 (m, 1H), 7.1 (d, J=8.2 Hz, 1H), 6.84-6.77 (m, 2H), 5.04 (s, 2H), 3.84 (s, 3H), 3.40-3.36 (m, 2H), 2.46-2.38 (m, 6H), 1.49-1.47 (m, 4H), 1.38-1.36 (m, 2H).

Example 8

3-(3-Methoxybenzyl)-2,4-dioxo-1,2,3,4-tetrahydro-quinazoline-7-carboxylic acid (2-piperidine-1-yl-ethyl)-amide (Compound 8)

1.6 g (50%) of 3-(3-methoxybenzyl)-2,4-dioxo-1,2,3,4-tetrahydro-quinazoline-7-carboxylic acid methyl ester was obtained in the same manner of Example 1, using dimethyl 2-aminoterephthalate (2.0 g, 9.6 mmol), triethylamine (0.6 mL, 4.8 mmol) and 1-(isocyanatomethyl)-3-methoxybenzene (1.7 mL, 11.47 mmol).

$^1$H NMR (300 MHz, DMSO-d$_6$) δ 11.74 (s, 1H), 8.06 (d, J=8.2 Hz, 1H), 7.78 (s, 1H), 7.71 (d, J=8.2 Hz, 1H), 7.21 (t, J=7.8 Hz, 1H), 6.88-6.81 (m, 3H), 5.06 (s, 2H), 3.90 (s, 3H), 3.71 (s, 3H).

From thus obtained ester (1.6 g, 4.7 mmol), 1.2 g (79%) of 3-(3-methoxybenzyl)-2,4-dioxo-1,2,3,4-tetrahydro-quinazoline-7-carboxylic acid was obtained in the same manner of Example 1.

$^1$H NMR (300 MHz, DMSO-d$_6$) δ 13.55 (s, 1H), 11.74 (s, 1H), 8.03 (d, J=8.2 Hz, 1H), 7.79 (s, 1H), 7.70 (dd, J=8.2 Hz, J=1.3 Hz, 1H), 7.22 (t, J=7.8 Hz, 1H), 6.87-6.80 (m, 3H), 5.06 (s, 2H), 3.71 (s, 3H).

From thus obtained acid (90 mg, 0.276 mmol), 55 mg (46%) of the target compound was obtained in the same manner of Example 7, using 2-piperidine-1-yl-ethylamine (78 μL, 0.552 mmol).

$^1$H NMR (300 MHz, DMSO-d$_6$) δ 11.67 (s, 1H), 8.80 (s, 1H), 8.00 (d, J=8.1 Hz, 1H), 7.59 (t, J=3.8 Hz, 2H), 7.21 (t, J=7.6 Hz, 1H), 6.86-6.80 (m, 3H), 5.05 (s, 2H), 3.71 (s, 3H), 3.39-3.37 (m, 2H), 2.42 (s, 6H), 1.50-1.46 (m, 4H), 1.38-1.36 (m, 2H).

Example 9

3-(4-Methoxybenzyl)-2,4-dioxo-1,2,3,4-tetrahydro-quinazoline-7-carboxylic acid (2-piperidine-1-yl-ethyl)-amide (Compound 9)

3.6 g (55%) of 3-(4-methoxybenzyl)-2,4-dioxo-1,2,3,4-tetrahydro-quinazoline-7-carboxylic acid methyl ester was obtained in the same manner of Example 1, using dimethyl 2-aminoterephthalate (4.0 g, 19.1 mmol), triethylamine (1.5 mL, 9.5 mmol) and 1-(isocyanatomethyl)-4-methoxybenzene (3.0 mL, 23.0 mmol).

$^1$H NMR (300 MHz, DMSO-d$_6$) δ 11.72 (s, 1H), 8.05 (d, J=8.2 Hz, 1H), 7.77 (s, 1H), 7.70 (d, J=8.2 Hz, 1H), 7.28 (d, J=8.5 Hz, 2H), 6.86 (d, J=8.5 Hz, 2H), 5.01 (s, 2H), 3.89 (s, 3H), 3.71 (s, 3H).

From thus obtained ester (3.6 g, 10.4 mmol), 2.9 g (86%) of 3-(4-methoxybenzyl)-2,4-dioxo-1,2,3,4-tetrahydro-quinazoline-7-carboxylic acid was obtained in the same manner of Example 1.

$^1$H NMR (300 MHz, DMSO-d$_6$) δ 11.71 (s, 1H), 8.05 (d, J=8.1 Hz, 1H), 7.79 (s, 1H), 7.71 (d, J=8.4 Hz, 1H), 7.31 (d, J=8.4 Hz, 2H), 6.88 (d, J=8.4 Hz, 2H), 5.03 (s, 2H), 3.72 (s, 3H).

From thus obtained acid (90 mg, 0.276 mmol), 83 mg (70%) of the target compound was obtained in the same manner of Example 7, using 2-piperidine-1-yl-ethylamine (78 μL, 0.552 mmol).

$^1$H NMR (300 MHz, DMSO-d$_6$) δ 11.63 (s, 1H), 8.57 (s, 1H), 7.99 (d, J=8.1 Hz, 1H), 7.57 (d, J=10.1 Hz, 2H), 7.28 (d, J=8.6 Hz, 2H), 6.85 (d, J=8.6 Hz, 2H), 5.01 (s, 2H), 3.70 (s, 3H), 3.37-3.34 (m, 2H), 2.44-2.36 (m, 6H), 1.48-1.36 (m, 6H).

Example 10

3-Cyclohexyl-2,4-dioxo-1,2,3,4-tetrahydro-quinazoline-7-carboxylic acid (2-piperidine-1-yl-ethyl)-amide (Compound 10)

Dimethyl 2-aminoterephthalate (3.0 g, 14.34 mmol) and triphosgene (5.1 g, 17.22 mmol) were dissolved in toluene. Stirring was carried out at 110° C. for 6 hours under reflux to obtain 2-isocyanato-terephthalic acid dimethyl ester. After evaporating solvent, the compound was dissolved in 1,4-dioxane and triethylamine in vacuum state. After adding cyclohexylamine (2.5 mL, 21.5 mmol), stirring was carried out at 90° C. for 60 hours under reflux. After the reaction was completed, the produced solid was filtered with ether to obtain 1.75 g (37%) of 2-(3-cyclohexyl-ureido)-terephthalic acid dimethyl ester having a urea structure.

$^1$H NMR (300 MHz, DMSO-d$_6$) δ 9.66 (s, 1H), 9.00 (s, 1H), 7.97 (d, J=8.2 Hz, 1H), 7.51-7.48 (m, 2H), 4.75 (bs, 1H), 3.88 (s, 3H), 3.86 (s, 3H), 2.38 (bs, 2H), 1.82-1.54 (m, 4H), 1.29-1.11 (m, 4H).

Thus obtained ester (1.51 g, 5.23 mmol) was dissolved in 10% NaOH/MeOH (⅓, w/w) and stirred at 70° C. for 3 hours. The progress and completion of the reaction were confirmed by TLC (CH$_2$Cl$_2$:MeOH=3:1). After the reaction was completed, white solid produced by acidification with strong hydrochloric acid was filtered to obtain 0.80 g (53%) of 3-cyclohexyl-2,4-dioxo-1,2,3,4-tetrahydro-quinazoline-7-carboxylic acid.

$^1$H NMR (300 MHz, DMSO-d$_6$) δ 13.47 (s, 1H), 11.50 (s, 1H), 7.99 (d, J=8.2 Hz, 1H), 7.71 (s, 1H), 7.65 (dd, J=8.2 Hz, J=1.3 Hz, 1H), 4.76-4.68 (m, 1H), 2.42-2.34 (m, 2H), 1.81-1.77 (m, 2H), 1.65-1.58 (m, 2H), 1.32-1.16 (m, 4H).

From thus obtained acid (90 mg, 0.312 mmol), 25 mg (20%) of the target compound was obtained in the same manner of Example 7, using 2-piperidine-1-yl-ethylamine (53 mL, 0.374 mmol).

$^1$H NMR (300 MHz, DMSO-d$_6$) δ 11.46 (s, 1H), 8.61 (bs, 1H), 7.96 (d, J=8.5 Hz, 1H), 7.55-7.53 (m, 2H), 4.72 (t, J=12 Hz, 1H), 3.38 (bs, 2H), 2.50-2.32 (m, 6H), 1.81-1.77 (m, 2H), 1.65-1.58 (m, 4H), 1.49 (bs, 4H), 1.37-1.16 (m, 6H).

Example 11

2,4-Dioxo-3-propyl-1,2,3,4-tetrahydro-quinazoline-7-carboxylic acid (2-piperidine-1-yl-ethyl)-amide (Compound 11)

0.70 g (50%) of 2-(3-propyl-ureido)-terephthalic acid dimethyl ester was obtained in the same manner of Example 10, using dimethyl 2-aminoterephthalate (1.0 g, 5.0 mmol) and triphosgene (1.7 g, 5.7 mmol), propylamine (0.82 mL, 10.0 mmol).

$^1$H NMR (300 MHz, DMSO-d$_6$) δ 9.73 (s, 1H), 9.00 (s, 1H), 7.99 (d, J=8.2 Hz, 1H), 7.58 (s, 1H), 7.53-7.49 (m, 1H), 3.89 (s, 3H), 3.86 (s, 3H), 3.05-2.96 (m, 2H), 1.45 (m, 2H), 0.88 (t, J=7.4 Hz, 3H).

From thus obtained ester (0.70 g, 2.38 mmol), 0.41 g (70%) of 2,4-dioxo-3-propyl-1,2,3,4-tetrahydro-quinazoline-7-carboxylic acid was obtained in the same manner of Example 10.

$^1$H NMR (300 MHz, DMSO-d$_6$) δ 13.76 (s, 1H), 11.86 (s, 1H), 8.28 (d, J=8.2 Hz, 1H), 8.01 (s, 1H), 7.94 (d, J=8.2 Hz, 1H), 4.11 (t, J=7.4 Hz, 2H), 1.91-1.79 (m, 2H), 1.14 (t, J=7.4 Hz, 3H).

From thus obtained acid (90 mg, 0.362 mmol), 30 mg (23%) of the target compound was obtained in the same manner of Example 1, using 2-piperidine-1-yl-ethylamine (73 mL, 0.434 mmol).

$^1$H NMR (300 MHz, CD$_3$OD) δ 8.12 (d, J=8.3 Hz, 1H), 7.63 (s, 1H), 7.61 (dd, J=7.8 Hz, J=1.4 Hz, 1H), 3.99 (t, J=7.5 Hz, 2H), 3.65 (t, J=6.6 Hz, 2H), 2.87-2.81 (m, 6H), 1.75-1.68 (m, 6H), 1.59-1.58 (m, 4H), 0.98 (t, J=7.5 Hz, 3H).

Example 12

3-Methyl-2,4-dioxo-1,2,3,4-tetrahydro-quinazoline-7-carboxylic acid (2-piperidine-1-yl-ethyl)-amide (Compound 12)

0.78 g (61%) of 2-(3-methyl-ureido)-terephthalic acid dimethyl ester was obtained in the same manner of Example 10, using dimethyl 2-aminoterephthalate (1.0 g, 5.0 mmol), triphosgene (1.7 g, 5.7 mmol) and methylamine (40% in water, 0.74 mL).

$^1$H NMR (300 MHz, DMSO-d$_6$) δ 9.75 (s, 1H), 8.99 (s, 1H), 7.99 (d, J=8.2 Hz, 1H), 7.53-7.50 (m, 1H), 7.44 (s, 1H), 3.89 (s, 3H), 3.86 (s, 3H), 2.65 (d, J=4.4 Hz, 3H).

From thus obtained ester (0.78 g, 2.93 mmol), 0.64 g (98%) of 3-methyl-2,4-dioxo-1,2,3,4-tetrahydro-quinazoline-7-carboxylic acid was obtained in the same manner of Example 10.

$^1$H NMR (300 MHz, DMSO-d$_6$) δ 13.50 (s, 1H), 11.61 (s, 1H), 8.02 (d, J=8.2 Hz, 1H), 7.75 (s, 1H), 7.68 (d, J=8.2 Hz, 1H), 3.25 (s, 3H).

From thus obtained acid (90 mg, 0.362 mmol), 70 mg (52%) of the target compound was obtained in the same manner of Example 1, using 2-piperidine-1-yl-ethylamine (70 mL, 0.490 mmol).

$^1$H NMR (300 MHz, DMSO-d$_6$) δ 11.65 (s, 1H), 8.64 (bs, 1H), 7.99 (d, J=8.3 Hz, 1H), 7.58 (s, 1H), 7.56 (d, J=8.0 Hz, 1H), 3.40-3.38 (m, 2H), 3.25 (s, 3H), 2.49 (bs, 6H), 1.52 (bs, 4H), 1.39 (bs, 2H).

Example 13

(2-Chloro-benzyl)-2,4-dioxo-1,2,3,4-tetrahydro-quinazoline-7-carboxylic acid (2-piperidine-1-yl-ethyl)-amide (Compound 13)

2.8 g (45%) of 3-(2-chloro-benzyl)-2,4-dioxo-1,2,3,4-tetrahydro-quinazoline-7-carboxylic acid methyl ester was obtained in the same manner of Example 1, using dimethyl 2-aminoterephthalate (3.7 g, 17.9 mmol), triethylamine (2.5 mL, 17.9 mmol) and 1-chloro-2-isocyanatomethylbenzene (3.0 mL, 20.6 mmol).

$^1$H NMR (300 MHz, DMSO-d$_6$) δ 11.80 (s, 1H), 8.07 (d, J=8.2 Hz, 1H), 7.82 (s, 1H), 7.74 (d, J=8.2 Hz, 1H), 7.48 (d, J=7.5 Hz, 1H), 7.31-7.21 (m, 2H), 7.07 (d, J=7.1 Hz, 1H), 5.13 (s, 2H), 3.91 (s, 3H).

From thus obtained ester (2.0 g, 5.7 mmol), 1.9 g (99%) of 3-(2-chloro-benzyl)-2,4-dioxo-1,2,3,4-tetrahydro-quinazoline-7-carboxylic acid was obtained in the same manner of Example 1.

$^1$H NMR (300 MHz, DMSO-d$_6$) δ 13.55 (s, 1H), 11.81 (s, 1H), 8.04 (d, J=8.2 Hz, 1H), 7.82 (s, 1H), 7.72 (d, J=8.2 Hz, 1H), 7.48 (d, J=7.5 Hz, 1H), 7.31-7.21 (m, 2H), 7.06 (d, J=7.1 Hz, 1H), 5.13 (s, 2H).

From thus obtained acid (90 mg, 0.272 mmol), 72 mg (60%) of the target compound was obtained in the same manner of Example 1, using 2-piperidine-1-yl-ethylamine (77 μL, 0.544 mmol).

$^1$H NMR (300 MHz, DMSO-d$_6$) δ 11.79 (s, 1H), 9.03-8.93 (m, 1H), 8.02 (d, J=6.1 Hz, 1H), 7.68-7.46 (m, 2H), 7.48-7.46 (m, 1H), 7.29-7.20 (m, 2H), 7.02-7.04 (m, 1H), 5.12 (s, 2H), 3.63-3.42 (m, 2H), 2.90-2.61 (m, 6H), 1.71-1.21 (m, 6H).

Example 14

3-(4-Chloro-benzyl)-2,4-dioxo-1,2,3,4-tetrahydro-quinazoline-7-carboxylic acid (2-piperidine-1-yl-ethyl)-amide (Compound 14)

65 mg (55%) of the target compound was obtained using 3-(4-chloro-benzyl)-2,4-dioxoquinazoline-7-carboxylic acid (90 mg, 0.272 mol) obtained in Example 1 and 2-piperidine-1-yl-ethylamine (85 mL, 0.598 mmol).

$^1$H NMR (400 MHz, DMSO-d$_6$) δ 11.62 (s, 1H), 8.59 (bs, 1H), 7.98 (d, J=8.2 Hz, 1H), 7.59-7.56 (m, 2H), 7.34 (bs, 4H), 5.05 (s, 2H), 3.36-3.34 (m, 2H), 2.43-2.36 (m, 6H), 1.47 (bs, 4H), 1.35 (bs, 2H).

Example 15

3-(4-Chloro-benzyl)-2,4-dioxo-1,2,3,4-tetrahydro-quinazoline-7-carboxylic acid (2-(2-methylpiperidine-1-yl)ethyl)-amide (Compound 15)

15 mg (12%) of the target compound was obtained in the same manner of Example 1, using 3-(4-chloro-benzyl)-2,4-dioxoquinazoline-7-carboxylic acid (90 mg, 0.272 mol) obtained in Example 1 and 2-(2-methyl-piperidine-1-yl)-ethylamine (77 mL, 0.544 mmol).

$^1$H NMR (400 MHz, DMSO-d$_6$) δ 11.69 (s, 1H), 8.61 (bs, 1H), 7.98 (d, J=8 Hz, 1H), 7.59-7.55 (m, 2H), 7.34 (bs, 4H), 5.05 (s, 2H), 3.38 (bs, 2H), 2.78-2.74 (m, 2H), 2.31 (bs, 1H), 2.26-2.22 (m, 2H), 1.55-1.39 (m, 4H), 1.21-1.18 (m, 2H), 1.00 (bs, 3H).

Example 16

3-(4-Chloro-benzyl)-2,4-dioxo-1,2,3,4-tetrahydro-quinazoline-7-carboxylic acid (3-morpholine-4-yl-propyl)-amide (Compound 16)

30 mg (25%) of the target compound was obtained in the same manner of Example 1, using 3-(4-chloro-benzyl)-2,4-dioxoquinazoline-7-carboxylic acid (90 mg, 0.272 mol) obtained in Example 1 and 3-morpholine-4-yl-propylamine (87 mL, 0.598 mmol).

$^1$H NMR (400 MHz, DMSO-d$_6$) δ 11.72 (s, 1H), 8.71 (bs, 1H), 7.98 (d, J=8.1 Hz, 1H), 7.66-7.57 (m, 2H), 7.34 (bs, 4H), 5.05 (s, 2H), 3.55 (bs, 4H), 3.27 (bs, 2H), 2.32 (bs, 6H), 1.67 (bs, 2H).

Example 17

3-(4-Chloro-benzyl)-2,4-dioxo-1,2,3,4-tetrahydro-quinazoline-7-carboxylic acid [3-(2-methyl-piperidine-1-yl)-propyl]-amide (Compound 17)

65 mg (52%) of the target compound was obtained in the same manner of Example 1, using 3-(4-chloro-benzyl)-2,4-dioxoquinazoline-7-carboxylic acid (90 mg, 0.272 mol) obtained in Example 1 and 3-(2-methyl-piperidine-1-yl)-propylamine (103 mL, 0.598 mmol).

$^1$H NMR (400 MHz, DMSO-d$_6$) δ 11.67 (s, 1H), 8.72 (bs, 1H), 7.99 (d, J=8.1 Hz, 1H), 7.59-7.55 (m, 2H), 7.34 (bs, 4H), 5.05 (s, 2H), 3.26-3.24 (m, 2H), 2.77-2.64 (m, 2H), 2.23 (bs, 2H), 2.04 (bs, 1H), 1.64-1.39 (m, 6H), 1.20 (bs, 2H), 0.96 (bs, 2H).

Example 18

3-(4-Chloro-benzyl)-2,4-dioxo-1,2,3,4-tetrahydro-quinazoline-7-carboxylic acid [3-(2-ethyl-piperidine-1-yl)-propyl]-amide (Compound 18)

55 mg (42%) of the target compound was obtained in the same manner of Example 1, using 3-(4-chloro-benzyl)-2,4-dioxoquinazoline-7-carboxylic acid (90 mg, 0.272 mmol)

obtained in Example 1 and 3-(2-ethyl-piperidine-1-yl)-propylamine (101 mL, 0.598 mmol).

$^1$H NMR (400 MHz, DMSO-d$_6$) δ 11.65 (s, 1H), 8.71 (bs, 1H), 7.99 (d, J=8.3 Hz, 1H), 7.59-7.55 (m, 2H), 7.34 (bs, 4H), 5.06 (s, 2H), 3.26-3.25 (m, 2H), 2.75-2.66 (m, 2H), 2.22 (bs, 1H), 2.12 (bs, 2H), 1.65-1.60 (m, 2H), 1.49-1.37 (m, 6H), 1.24-1.22 (m, 2H), 0.78 (t, J=7.2 Hz, 2H).

Example 19

3-(4-Chloro-benzyl)-2,4-dioxo-1,2,3,4-tetrahydro-quinazoline-7-carboxylic acid (3-piperidine-1-yl-propyl)-amide (Compound 19)

55 mg (45%) of the target compound was obtained in the same manner of Example 1, using 3-(4-chloro-benzyl)-2,4-dioxoquinazoline-7-carboxylic acid (90 mg, 0.272 mol) obtained in Example 1 and 3-piperidine-1-yl-propylamine (85 mL, 0.598 mmol).

$^1$H NMR (400 MHz, DMSO-d$_6$) δ 11.63 (s, 1H), 8.72 (bs, 1H), 7.98 (d, J=8 Hz, 1H), 7.59-7.55 (m, 2H), 7.34 (bs, 4H), 5.05 (s, 2H), 3.27-3.25 (m, 2H), 2.27 (bs, 6H), 1.65 (bs, 2H), 1.45 (bs, 4H), 1.34 (bs, 2H).

TEST EXAMPLES

Test Example 1

Assay for 5-HT$_3$A Receptor

Antagonistic activity of the quinazoline derivatives represented by Formula 1 against the 5-HT$_3$A receptor was identified.

Although the results for only some of the quinazoline derivatives represented by Formula 1 listed in Table 1 are given, other compounds represented by Formula 1 are believed to exhibit identical or similar antagonistic activity against the 5-HT$_3$A receptor.

1) Culturing and Isolation of *Xenopus* Oocytes

*Xenopus laevis* (African clawed frog) was anesthetized with ice and follicular oocytes were taken out after incising the lateral abdominal region. The follicular oocytes were washed with Ca$^{2+}$-free OR2 solution (82.5 mM NaCl, 2 mM KCl, 1 mM MgCl$_2$, 5 mM HEPES buffer, 2.5 mM sodium pyruvate, penicillin 100 units/mL and streptomycin 100 μg/mL). Then, after addition of 2 mg/mL collagenase to the solution followed by about 2 hours of gentle shaking, only the oocytes of stages V and VI which have lost their follicles were selected. These oocytes were washed several times with ND96 media (pH 7.5 solution containing 96 mM NaCl, 2 mM KCl, 1 mM MgCl$_2$, 1.8 mM CaCl$_2$, 5 mM HEPES, 0.5 mM theophylline and 50 μg/mL gentamycin) and cultured in an incubator of 16 to 18° C. The medium was exchanged every day, and all the experiments were performed within 2 to 6 days after the isolation of the oocytes.

2) Recording of 5-HT$_3$A Receptor Channel Activity

The oocytes were placed in a small 0.5 mL Plexiglas net chamber and superfused in a solution (ND96 medium) containing the test compound or not. Microelectrodes were filled with 3 M KCl and resistance was adjusted to about 0.2 to 0.7 MΩ. Most of the electrophysiological experiments were carried out while holding the oocytes such that the holding potential was maintained at −100 mV for a duration of 2000 seconds. During the current-voltage experiments, the voltage was increased from −100 mV to +60 mV, by 10 mV. During the time course experiments, Na$^+$ current was induced by evoking from −100 mV to −10 mV for 20 ms. Two-electrode voltage-clamp recordings were carried out using an oocyte clamp (OC-725C, Warner Instrument) connected to Digidata 1200B [Choi, S., Jung, S. Y., Lee, J. H., Sala, F., Criado, M., Mulet, J., Valor, L. M., Sala, S., Engel, A. G. and Nah, S. Y. (2002) *Eur. J. Pharmacol.* 442, 37-45].

3) Oocyte Injection cRNAs of 5-HT$_3$A receptors existing in the nervous system (3-5 ng/oocyte, each) were injected into the oocytes. Oocyte injection was carried out using Nanoject Automatic Oocyte Injector (Drummond Scientific, Broomall, Pa.), 40 to 50 nL at once. Oocyte volume was assumed to be approximately 1 μL.

4) Expression of 5-HT$_3$A Receptor in *Xenopus* Oocytes

*E. coli* was transformed with the plasmids having the 5-HT$_3$A receptor channels existing in the nervous system. Then, cDNAs having 5-HT$_3$A receptors were prepared using Miniprep kit (Promega). After linearization using restriction enzymes, cRNAs for 5-HT$_3$A receptor channels were prepared using in vitro transmission kit (Promega or Ambion).

50% inhibitory concentration (IC$_{50}$), maximum inhibition value (V$_{max}$) and Hill coefficient (nH) of the quinazoline derivative prepared in the present invention for the serotonin 5-HT$_3$A receptor were calculated. The result is given in the following Table 1. Concentrations of the compounds were 0.01, 0.03, 0.1, 0.3, 1, 3, 10 and 100 μM, or 0.003, 0.01, 0.03, 0.1, 0.3, 1, 3 and 10 μM, depending on their efficiency. IC$_{50}$, V$_{max}$ and Hill coefficient for each compound were obtained from concentration-response curves.

TABLE 1

| Compounds | | V$_{max}$ | IC$_{50}$ | nH |
|---|---|---|---|---|
| 1 | (structure) | 103.2 ± 12.8 | 7.5 ± 2.5 | 0.9 ± 0.1 |

TABLE 1-continued
| | Compounds | $V_{max}$ | $IC_{50}$ | nH |
|---|---|---|---|---|
| 2 | 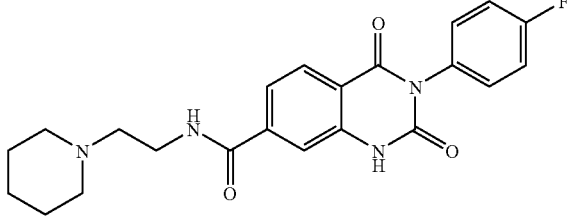 | 107.9 ± 6.0 | 1.9 ± 0.4 | 0.9 ± 0.1 |
| 3 | 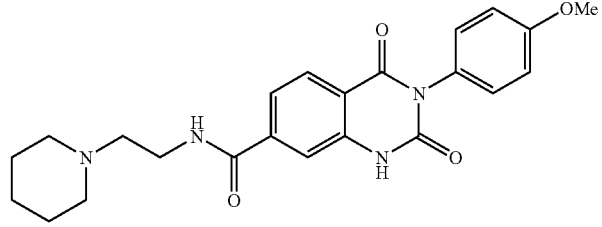 [SMILES: COc1ccc(-n2c(=O)[nH]c3cc(C(=O)NCCN4CCCCC4)ccc3c2=O)cc1] | 100.6 ± 3.6 | 1.6 ± 0.2 | 1.4 ± 0.2 |
| 4 | 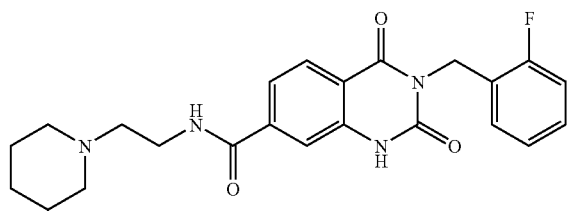 [SMILES: O=C(NCCN1CCCCC1)c1ccc2c(=O)n(Cc3ccccc3F)c(=O)[nH]c2c1] | 100.2 ± 9.6 | 2.1 ± 0.6 | 1.4 ± 0.4 |
| 5 | 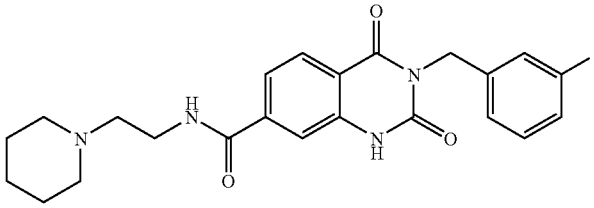 | 107.5 ± 11.5 | 2.4 ± 0.8 | 1.0 ± 0.2 |
| 6 | 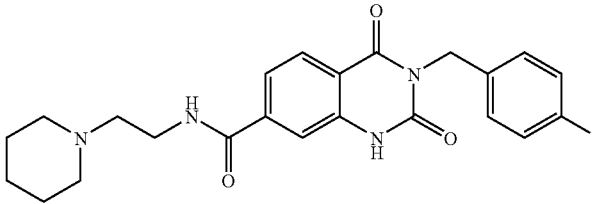 | 104.6 ± 7.5 | 1.9 ± 0.4 | 1.0 ± 0.2 |
| 7 | 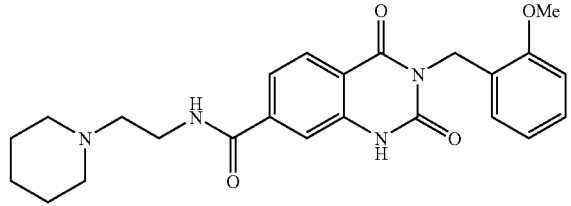 [SMILES: COc1ccccc1Cn1c(=O)[nH]c2cc(C(=O)NCCN3CCCCC3)ccc2c1=O] | 103.1 ± 5.1 | 1.4 ± 0.2 | 1.1 ± 0.2 |
| 8 | 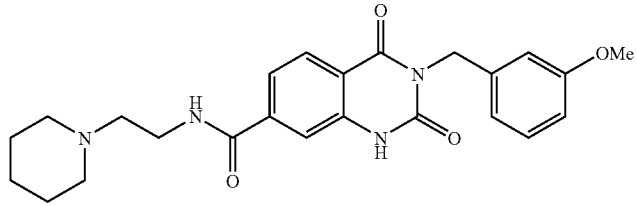 [SMILES: COc1cccc(Cn2c(=O)[nH]c3cc(C(=O)NCCN4CCCCC4)ccc3c2=O)c1] | 107.4 ± 8.5 | 2.7 ± 0.6 | 1.3 ± 0.3 |

TABLE 1-continued

| Compounds | $V_{max}$ | $IC_{50}$ | nH |
|---|---|---|---|
| 9 (piperidine-ethyl-NH-C(O)-quinazolinedione-N-CH2-C6H4-OMe) | 96.4 ± 2.9 | 0.8 ± 0.1 | 1.7 ± 0.2 |
| 10 (piperidine-ethyl-NH-C(O)-quinazolinedione-N-cyclohexyl) | 98.8 ± 4.2 | 2.0 ± 0.3 | 1.1 ± 0.1 |
| 11 (piperidine-ethyl-NH-C(O)-quinazolinedione-N-propyl) | 103.7 ± 3.6 | 2.2 ± 0.2 | 1.3 ± 0.1 |
| 12 (piperidine-ethyl-NH-C(O)-quinazolinedione-N-methyl) | 103.2 ± 3.3 | 2.2 ± 0.2 | 1.4 ± 0.1 |
| 13 (piperidine-ethyl-NH-C(O)-quinazolinedione-N-CH2-C6H4-2-Cl) | 96.0 ± 3.9 | 2.1 ± 0.2 | 1.8 ± 0.3 |
| 14 (piperidine-ethyl-NH-C(O)-quinazolinedione-N-CH2-C6H4-4-Cl) | 106.4 ± 2.5 | 3.3 ± 0.5 | 1.2 ± 0.2 |
| 15 (2-methylpiperidine-ethyl-NH-C(O)-quinazolinedione-N-CH2-C6H4-4-Cl) | 104.0 ± 2.5 | 2.8 ± 0.2 | 1.2 ± 0.1 |

TABLE 1-continued

| Compounds | | $V_{max}$ | $IC_{50}$ | nH |
|---|---|---|---|---|
| 16 | [structure] | 52.5 ± 0.6 | 1.3 ± 0.1 | 5.3 ± 1.5 |
| 17 | [structure] | 86.5 ± 11.5 | 5.9 ± 2.5 | 1.1 ± 0.4 |
| 18 | [structure] | 99.5 ± 1.6 | 4.8 ± 0.2 | 1.4 ± 0.1 |
| 19 | [structure] | 98.2 ± 4.5 | 5.7 ± 0.6 | 1.5 ± 0.2 |
| Control | MDL72222 | 99.6 ± 7.7 | 0.77 ± 0.16 | 1.25 ± 0.2 |

As seen in Table 1, the *Xenopus laevis* oocytes treated with the compounds of the present invention were confirmed to inhibit the inward current (I5-HT) induced by 5-HT (1 μM), when measured by the two-electrode voltage clamp assay technique.

Test Example 2

Toxicity Test

In order to identify toxicity of the quinazoline derivatives represented by Formula 1 according to the present invention, 1 to 20 mg of the compounds were intra-abdominally administered to 24 mice. Behaviors of the mice were monitored for 24 hours and survival was observed 24 hours later.

As a result, the quinazoline derivatives of the present examples had no toxicity problem at all. Of the six mice to which 20 mg was administered, three survived and the other three were sacrificed. In contrast, all the mice survived when the administration dose was less than 20 mg. No statistically significant change was observed in behavior monitoring between the mice to which the compounds were administered and not. Based on the experiment result, the toxic dose of the quinazoline derivatives at which approximately half of the mice survive ($TD_{50}$) can be calculated at 20 mg (1 mg/g).

Test Example 3

Preparation of Tablet

Tablets for oral administration were prepared by wet granulation and dry granulation using the quinazoline derivative represented by Formula 1 according to the present invention as active ingredient.
Composition:
Active ingredient 200 mg, light anhydrous silica acid 10 mg, magnesium stearate 2 mg, microcrystalline cellulose 50 mg, sodium starch glycolate 25 mg, cornstarch 113 mg, anhydrous ethanol adequate.

Test Example 4

Preparation of Ointment

Ointments were prepared using the quinazoline derivative represented by Formula 1 according to the present invention as active ingredient.
Composition:
Active ingredient 5 g, cetyl palmitate 20 g, cetanol 40 g, isopropyl myristate 80 g, sorbitan monostearate 20 g, polysorbate 60 g, propyl p-hydroxybenzoate 1 g, methyl p-hydroxybenzoate 1 g, phosphoric acid and purified water adequate.

Test Example 5

Preparation of Injection

Injections were prepared using the quinazoline derivative represented by Formula 1 according to the present invention as active ingredient.
Composition:
Active ingredient 100 mg, mannitol 180 mg, sodium hydrogen phosphate 25 mg, injection for water 2974 mg Test Example 6

Preparation of Drink

Drink compositions were prepared by dissolving 500 mg of the quinazoline derivative represented by Formula 1 according to the present invention in adequate amount of water, vitamin C, as supplementary ingredient, adding adequate amount of citric acid, sodium citrate and oligosaccharide, as favor enhancer, and adding adequate amount of sodium benzoate, as preservative, and further adding water to make 100 mL. As occasion demands, taurine, myoinositol, folic acid, pantothenic acid, etc. may be added alone or in combination.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

What is claimed is:
1. A method of treating emesis or nausea in a subject comprising administering to the subject an effective amount of one or more quinazoline compounds represented by formula (1) or a pharmaceutically acceptable salt thereof:

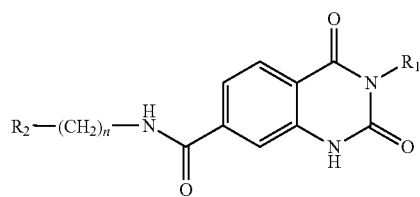

(1)

wherein:
$R_1$ is hydrogen, $C_1$-$C_6$ alkyl, phenyl or benzyl;
$R_2$ is a heterocyclic group selected from the group consisting of morpholine, pyrrolidine and piperidine;
wherein said phenyl or benzyl are optionally substituted by a substituent selected from the group consisting of halogen, $C_1$-$C_6$ alkyl and $C_1$-$C_6$ alkoxy; and
n is an integer from 1 to 6.
2. The method of claim 1, wherein:
R1 is hydrogen, methyl, ethyl, propyl, isopropyl, butyl, isobutyl, cyclobutyl, pentyl, isopentyl, cyclopentyl, hexyl, isohexyl, cyclohexyl; phenyl; phenyl substituted by a substituent selected from the group consisting of methyl, ethyl, propyl, isopropyl, butyl, isobutyl, cyclobutyl, pentyl, isopentyl, cyclopentyl, hexyl, isohexyl, cyclohexyl, fluoro, chloro, bromo, iodo, methoxy, ethoxy, propoxy, butoxy, pentoxy and hexyloxy; benzyl; or benzyl substituted by a substituent selected from the group consisting of methyl, ethyl, propyl, isopropyl, butyl, isobutyl, cyclobutyl, pentyl, isopentyl, cyclopentyl, hexyl, isohexyl, cyclohexyl, fluoro, chloro, bromo, iodo, methoxy, ethoxy, propoxy, butoxy, pentoxy, and hexyloxyl;
R2 is morpholine, pyrolidine or piperidine, and n is an integer from 1 to 6.
3. The method as set forth in claim 1, wherein the one or more compounds are selected from the group consisting of:
3-(4-chloro-benzyl)-2,4-dioxo-1,2,3,4-tetrahydro-quinazoline-7-carboxylic acid (2-pyrrolidine-1-yl-ethyl)-amide,
3-(4-fluoro-phenyl)-2,4-dioxo-1,2,3,4-tetrahydro-quinazoline-7-carboxylic acid (2-piperidine-1-yl-ethyl)-amide,
3-(4-methoxy-phenyl)-2,4-dioxo-1,2,3,4-tetrahydro-quinazoline-7-carboxylic acid (2-piperidine-1-yl-ethyl)-amide,
3-(2-fluoro-benzyl)-2,4-dioxo-1,2,3,4-tetrahydro-quinazoline-7-carboxylic acid (2-piperidine-1-yl-ethyl)-amide,
3-(3-fluoro-benzyl)-2,4-dioxo-1,2,3,4-tetrahydro-quinazoline-7-carboxylic acid (2-piperidine-1-yl-ethyl)-amide,
3-(4-fluoro-benzyl)-2,4-dioxo-1,2,3,4-tetrahydro-quinazoline-7-carboxylic acid (2-piperidine-1-yl-ethyl)-amide,
3-(2-methoxy-benzyl)-2,4-dioxo-1,2,3,4-tetrahydro-quinazoline-7-carboxylic acid (2-piperidine-1-yl-ethyl)-amide,
3-(3-methoxybenzyl)-2,4-dioxo-1,2,3,4-tetrahydro-quinazoline-7-carboxylic acid (2-piperidine-1-yl-ethyl)-amide,
3-(4-methoxybenzyl)-2,4-dioxo-1,2,3,4-tetrahydro-quinazoline-7-carboxylic acid (2-piperidine-1-yl-ethyl)-amide,
3-cyclohexyl-2,4-dioxo-1,2,3,4-tetrahydro-quinazoline-7-carboxylic acid (2-piperidine-1-yl-ethyl)-amide,
2,4-dioxo-3-propyl-1,2,3,4-tetrahydro-quinazoline-7-carboxylic acid (2-piperidine-1-yl-ethyl)-amide,
3-methyl-2,4-dioxo-1,2,3,4-tetrahydro-quinazoline-7-carboxylic acid (2-piperidine-1-yl-ethyl)-amide,
(2-chloro-benzyl)-2,4-dioxo-1,2,3,4-tetrahydro-quinazoline-7-carboxylic acid (2-piperidine-1-yl-ethyl)-amide,
3-(4-chloro-benzyl)-2,4-dioxo-1,2,3,4-tetrahydro-quinazoline-7-carboxylic acid (2-piperidine-1-yl-ethyl)-amide,
3-(4-chloro-benzyl)-2,4-dioxo-1,2,3,4-tetrahydro-quinazoline-7-carboxylicacid (2-(2-piperidine-1-yl) ethyl)-amide,
3-(4-chloro-benzyl)-2,4-dioxo-1,2,3,4-tetrahydro-quinazoline-7-carboxylicacid (3-morpholine-4-yl-propyl)-amide,
3-(4-chloro-benzyl)-2,4-dioxo-1,2,3,4-tetrahydro-quinazoline-7-carboxylic acid [3-(2-methyl-piperidine-1-yl)-propyl]-amide,
3-(4-chloro-benzyl)-2,4-dioxo-1,2,3,4-tetrahydro-quinazoline-7-carboxylic acid [3-(2-ethyl-piperidine-1-yl)-propyl]-amide, and
3-(4-chloro-benzyl)-2,4-dioxo-1,2,3,4-tetrahydro-quinazoline-7-carboxylic acid (3-piperidine-1-yl-propyl)-amide.
4. The method of claim 1, wherein the one or more quinazoline compounds are administered in a composition.
5. The method of claim 4, wherein the composition is in a form suitable for administration by injection.
6. The method of claim 4, wherein the composition is in a form suitable for parenteral administration.

7. The method of claim 1, wherein in formula (1), R1 is lower alkyl, cyclohexyl or benzyl substituted by halo or methoxy.

8. The method of claim 1, wherein 10 to 500 mg of the one or more quinazoline compounds are administered per day.

9. The method of claim 4, wherein the composition is contained in a health food.

10. The method of claim 1, wherein said emesis or nausea is associated with cancer chemotherapy, alcoholism, drug abuse or pregnancy.

* * * * *